United States Patent [19]
Tolosa et al.

[11] 4,003,151
[45] Jan. 18, 1977

[54] TEST PLATE READER

[75] Inventors: Felix P. Tolosa; Miles G. Hossom, both of Alexandria, Va.

[73] Assignee: Dynatech Laboratories, Incorporated, Alexandria, Va.

[22] Filed: Oct. 3, 1975

[21] Appl. No.: 619,183

[52] U.S. Cl. .................................................. 40/106.1
[51] Int. Cl.² ........................................ G09F 13/10
[58] Field of Search ............. 356/103, 244; 350/89, 350/87; 40/106.1, 86 A, 63 A

[56] References Cited
UNITED STATES PATENTS

| 2,157,437 | 5/1939 | Shipley, Jr. ........................ 350/89 |
| 2,332,668 | 10/1943 | Richards ............................. 350/89 |
| 3,425,148 | 2/1969 | Reese ............................. 40/106.1 X |

FOREIGN PATENTS OR APPLICATIONS

| 236,262 | 6/1945 | Switzerland ........................ 350/89 |
| 594,373 | 11/1947 | United Kingdom ................ 350/87 |

Primary Examiner—Louis G. Mancene
Assistant Examiner—John H. Wolff
Attorney, Agent, or Firm—Strauch, Nolan, Neale, Nies & Kurz

[57] ABSTRACT

A test plate reader wherein a transparent test plate having a multiplicity of material containing wells is located across a light path, and a target having a pattern of opaque areas corresponding in number and location to the wells is interposed in the light path between the light source and the plate, so that the wells may be viewed against a brighter uniformly lighted background for improved contrast.

9 Claims, 8 Drawing Figures

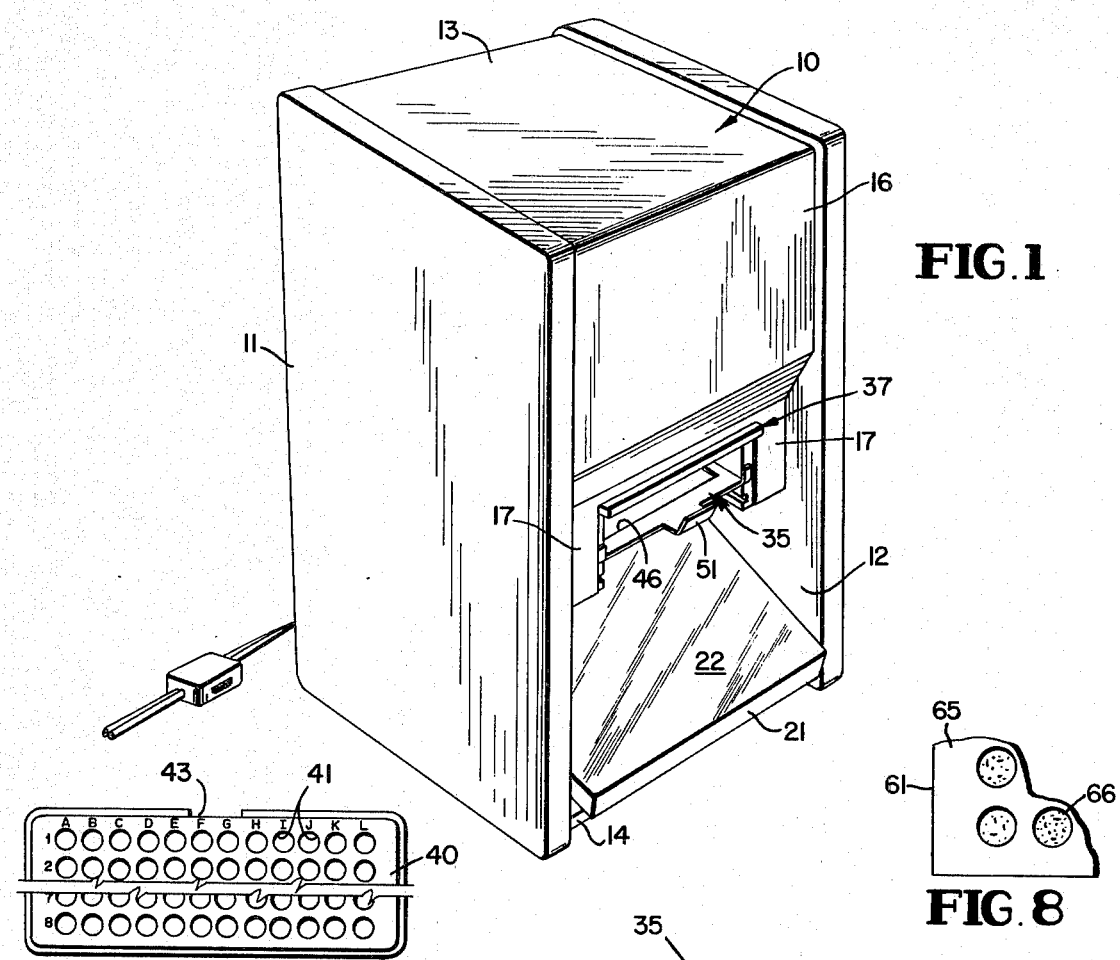
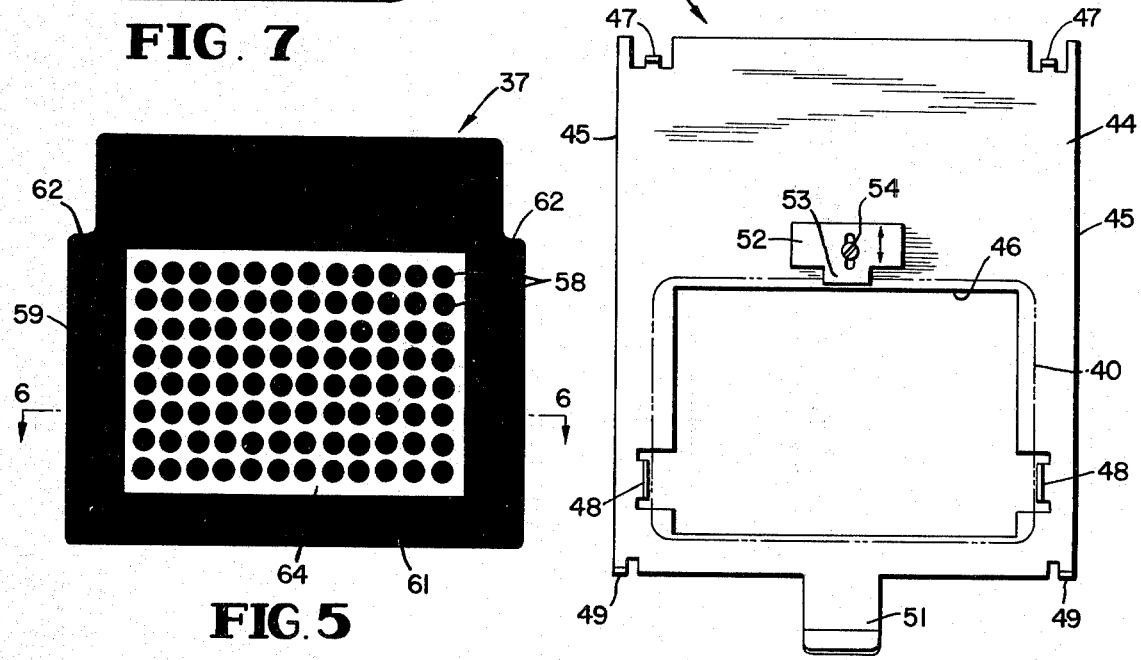

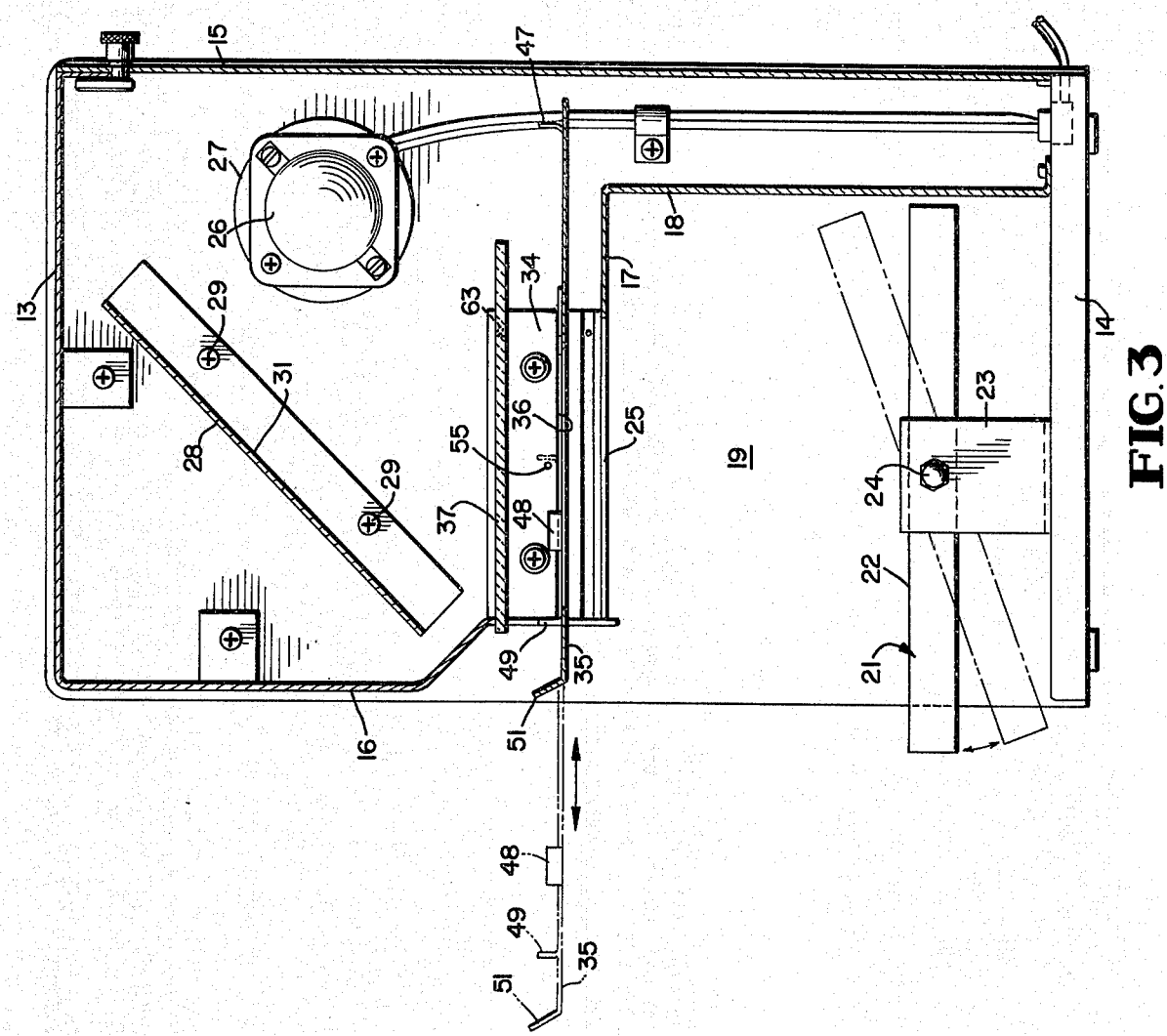
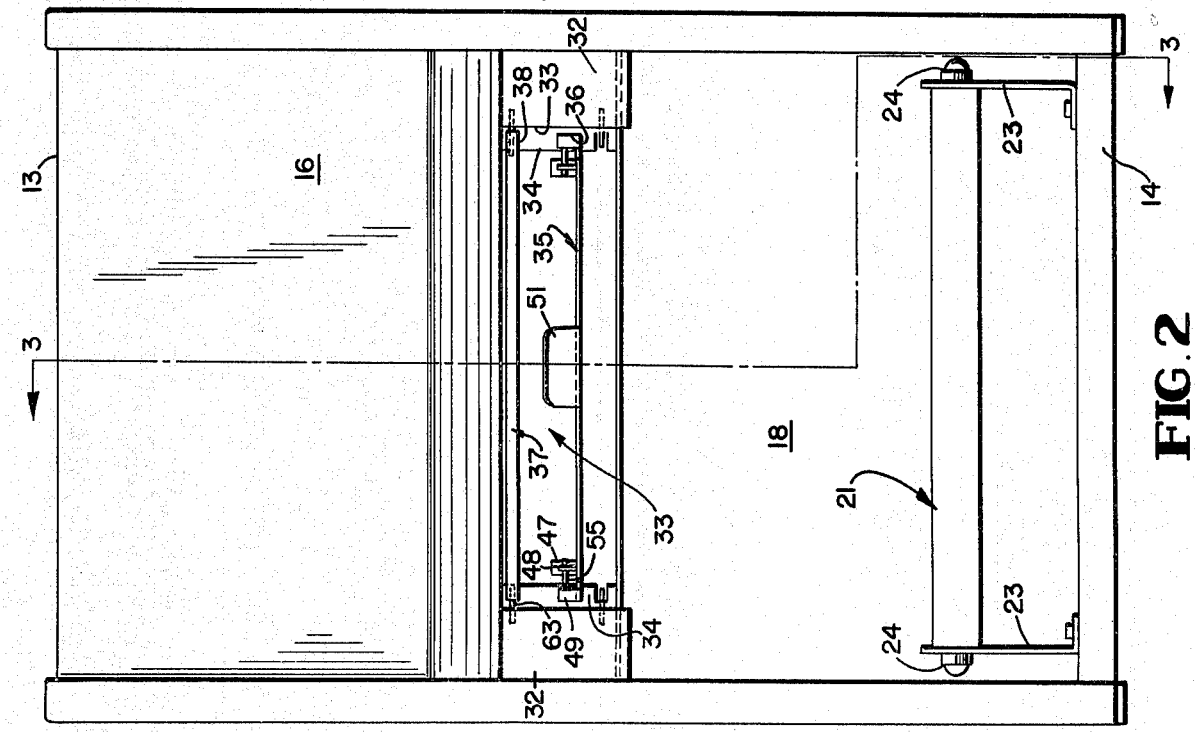

TEST PLATE READER

This invention relates to illuminated viewing devices and particularly to such devices wherein a test plate having a multiplicity of cells or wells each containing a specimen is viewed against a special illuminated background providing optimum contrast conditions, and a special method of illuminating the test plate.

In its preferred embodiment the invention will be disclosed as incorporated in an illuminated so-called test plate reader, wherein a transparent test plate or tray having a multiplicity, for example ninety six, of individual wells arranged in indexed order is viewed, as for detecting and/or measuring changes or transient differences in the contents of each well.

Apparatus for dispensing material into the wells of such test plates is known as disclosed in U.S. Pat. No. 3,650,306 issued Mar. 21, 1972 to Lancaster. After deposit of the material into the plates, they may be stored for a while and taken out and viewed periodically to detect reactions, bacteria growth or other changes, and the present invention is primarily directed to improved readers for such viewing operations.

Prior to the invention, it was conventional to pass diffused light through the test plate and view a reflected image of the underside of the plate. While this is quite satisfactory for certain purposes, there are difficulties in visually observing certain conditions, particularly where contrast is low and the change is small, and it is the major object of this invention to provide a plate reader of novel construction and mode of operation wherein each illuminated test plate well is viewed under optimum contrast conditions.

Another object of the invention is to provide a novel test plate reader device and method of illumination wherein a special background modifying target is interposed between the light source and the test plate.

A further object of the invention is to provide a novel test plate reader device wherein the test tray is mounted in a special slidable carrier interposed between the light source and the viewing station.

Another object of the invention is to provide a novel test plate reader wherein opaque or substantially opaque areas corresponding in number and location to the number and location of wells in the test plate are interposed in the light path adjacent the plate at the opposite side from the viewing station. Pursuant to this object special indexing arrangements are provided for ensuring known disposition of the test plate wells and accurate alignment of said areas.

It is a further object of the invention to provide a novel target for a test plate reader consisting of a thin transluscent plate modified to pass diffused light and having a multiplicity of substantially individual opaque areas that correspond in number and location to the wells in a test plate.

Further novel features and other objects of this invention will become apparent from the following detailed description, discussion and the appended claims taken in conjunction with the accompanying drawings.

BRIEF DESCRIPTION OF DRAWINGS

FIG. 1 is a general perspective view showing the invention in a preferred embodiment;

FIG. 2 is a front elevation of the housing;

FIG. 3 is a section on line 3—3 of FIG. 2 showing detail;

FIG. 4 is a top plan view of the test plate carrier apart from the housing;

FIG. 5 is a bottom plan view of the target element apart from the housing;

FIG. 6 is a section substantially on line 6—6 of FIG. 5, but showing the target in its normal top to bottom disposition;

FIG. 7 is an illustrative plan view of a conventional test plate; and

FIG. 8 is a fragmentary view diagramatically showing the illuminated image field viewed in the reflector by the user.

PREFERRED EMBODIMENTS

FIG. 1 shows a housing 10 having opposite side walls 11 and 12, top wall 13 and a bottom wall 14. The housing rear wall 15 is shown in FIG. 3. At the front side there is a partial front wall 16 at the top joined (FIG. 3) to a transverse horizontal internal wall 17 that connects to a transverse vertical internal wall 18 secured at its lower end to bottom wall 14. This provides a forwardly open space 19 extending across the lower part of the housing.

A reflector member 21 having an upper reflecting surface 22 is pivotally mounted in space 19 on brackets 23 upstanding from bottom wall 14 near the side walls. The pivot axis of reflector 21 is horizontal and it has friction tight journals 24 in the brackets that permit it to be moved to and maintained in a desired position of inclination within space 19.

Above reflector 21, wall 17 is apertured as indicated at 25 in FIG. 3, the area of such aperture being equal at least to a test plate to be read in the apparatus, as will appear.

The upper part of the housing contains a light source in the form of a standard lamp bulb 26 mounted in a socket 27. A reflector 28 secured to opposite side walls above aperture 25 as by screws 29 and is disposed at about 45° to horizontal. Reflector 28 is preferably a sheet of aluminum polished on surface 31.

Lamp 26 is substantially centered with respect to reflector surface 31 which in turn is of such area that the light deflected thereby in a vertically downward path has a cross sectional area at least equal to that of aperture 25 and preferably somewhat greater.

As shown the lower end of front wall 16 is offset inwardly and centrally apertured to provide extensions 32 disposed at opposite sides of an opening indicated at 33 in FIG. 2, and fixed guide blocks 34 are mounted on the side walls behind these extensions. As shown in FIGS. 1 and 3, a test plate carrier 35 is slidably mounted in a lower set of guide block grooves 36 and a special target 37 is slidably mounted in an upper set of guide blocks grooves 38.

Preferably guide blocks 34 are of nylon or some material having good low friction bearing characteristics, and the groove sets 36 and 38 are adjacent, parallel and horizontal.

A preferred form of carrier 35 is shown in FIG. 4, a modified standard form of test plate 40 is shown in FIG. 7, and a preferred form of target 37 is shown in FIGS. 5 and 6. The test plate is indicated for disclosure purposes in its normal reading location on the carrier in chain lines in FIG. 4.

The test plate 40 is preferably a molded transparent plastic multi-well generally flat unit mainly as disclosed in said Lancaster patent, to which reference may be made for further detail. Each upwardly open well 41 is preferably of the same size, the wells are evenly spaced in rows, and the rows are indexed as shown. At one edge of the plate, the rear side in FIG. 7, a recess 43 of predetermined size and shape is formed, for a purpose to appear.

Carrier 35 is preferably a thin flat opaque body 44 of sheet metal having parallel side edges 45 and a generally rectangular aperture 46 over which the test plate is positioned in the assembly in operation as indicated in FIG. 4. Body 44 is formed with upstanding parallel rear tabs 47, upstanding parallel side tabs 48, upstanding parallel front tabs 49 and a forwardly extending handle tab 51, all of these tabs being integral bent sections of the body sheet.

A sheet metal plate stop and locating element 52 is centrally mounted on the upper surface of plate body 44 at the rear edge of aperture 46. The arrangement is such that test plate 40 seats flat on the upper surface of carrier body 44 and is slidably displaced between side tabs 48 that are spaced to closely snugly slidably guide the plate which during insertion moves rearwardly until plate recess 43 interfits with a correspondingly shaped projection 53 on element 52 as shown in FIG. 4. Element 52 may be adjusted, as by the set screw and slot arrangement at 54 to preset the limit of rearward displacement of the test plate on the carrier. In some forms projection 53 may be integrally formed on the rear edge of aperture 46.

The area of aperture 46 which will be centered above the reflector 21 in operation is such that with the test plate in operative position as shown in FIGS. 3 and 4 an image of the undersides of all of the test wells will be visible in the reflector, as will appear. By providing the recess 43 and interfitting locator 53, it is ensured that the test plate may be positioned and displaced rearwardly on the carrier into only one operative location. This is important because of the indexed test wells, and eliminates a possible source of error in reading as will appear.

Thus in operation the operator merely pulls out carrier 35 fully until arrested by stop pins 55 as shown in FIG. 3, slides the test plate 40 (with recess 43 at the rear) rearwardly until it abuts and interfits with projection 53 and then slides the carrier rearwardly into the housing until front tabs 49 engage the parallel front faces of blocks 34. This locates the test plate in exact operative position over aperture 25 and in the light path to the reflector 21. When the carrier is pulled out fully rear tabs 47 engage side wall pins 55 to prevent undesired separation.

Target 37 preferably comprises a thin sheet of clear glass or plastic 56 having one surface 57 etched or sandblasted to be matt, whereby to diffuse the light passing therethrough. The matt surface 57 is the upper surface of the target as it is used in the assembly. The lower surface is provided with a multiplicity of identical opaque areas 58 that correspond in number, distribution and preferably size to the wells of the test plate 40. An opaque border area 59 is also provided on the lower surface surrounding the inner region containing the opaque areas 58, and the inner periphery 61 of the border area appears as a rectangular outline confining the inner region, with the area of that outline corresponding in plan to the area of the test plate.

As shown in FIG. 5 the target has laterally aligned rear shoulders 62 that (FIGS. 2 and 3) abut against fixed side pins 63 in the assembly, whereby to accurately position the target above the test plate when the target is slidably introduced along grooves 38.

In use of the reader device a target 37 having an opaque area pattern that corresponds to the test plate to be read is pushed in on grooves 38 until shoulders 62 abut pins 63. This locates the target with outline 61 in the vertical light path and exactly aligned with aperture 25 below. The test plate 40 is inserted in proper orientation and pushed to rearward position on pulled-out carrier 35, and then the carrier is pushed in as far as it will go as limited by engagement of tabs 49 with blocks 34. If the plate 40 is properly mounted on the carrier, that is with recess 43 receiving projection 53, each opaque area 58 of the target will be vertically aligned with a well 41 of the test plate. If the test plate is improperly oriented, such can be detected right away and corrected by reversing it front for rear on the carrier.

With lamp 26 energized, the light flux reflected from surface 31 and directly arriving from the lamp will be diffused substantially uniformly across the target, and light is transmitted through the non-opaque target area 64 within outline 61.

Referring to FIG. 8 which diagramatically shows a fragment of the virtual image viewed by the operator making the test, there will appear an outline corresponding to that at 61 of the target extending around a region consisting of a substantially uniformly brightly lighted background area 65 having therewith less brightly illuminated areas 66 corresponding to the test cells. These less brightly illuminated areas exhibit in remarkably and unexpectedly clear contrast particles, strains, bacteria and the like in the test cells having good visibility against the brighter background 65.

It is our theory that by preventing direct transmission of light through the individual test wells, the invention utilizes the stray side light which permeates the wells by transmission through the transparent walls of the wells to internally illuminate the wells and thereby present an attention focusing brightness difference with respect to the surrounding brighter background.

In practice it is preferable that target areas 58 be black, as by ink deposits or a silk-screen process. It is possible however that areas 58 and 59 may be of different light transmission values or area colors for certain test purposes. Therefore the term "substantially opaque" is used in the claims to denote any operative transmission reduction ranging from fully opaque to a desired value. Similarly areas 58 are preferably of the same size as well areas 41, but they may be slightly smaller or larger, and they are always fairly well centered with respect to the wells.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. Apparatus for viewing the wells of a transparent test plate having a multiplicity of individual test material containing wells arranged in predetermined relative location, comprising means including a light source defining a light path, means for mounting said test plate in predetermined location in said path, and a target mounted across said light path between the source and said test plate, said target having a multiplicity of individual substantially opaque areas corresponding in number and relative location to the number and relative location of the wells in the test plate.

2. The apparatus defined in claim 1, wherein said target is removably mounted whereby targets having patterns of substantially opaque areas corresponding to different patterns of wells in test plates may be selectively mounted in the apparatus.

3. The apparatus defined in claim 1, wherein said target areas are on a side of the target adjacent and parallel to said test plate.

4. The apparatus defined in claim 1, wherein a slidable carrier is provided for said test plate.

5. The apparatus defined in claim 4, wherein said carrier is provided with a formation for interfitting with a corresponding formation on the test plate, whereby the latter has only one operative location on the carrier.

6. The apparatus defined in claim 1, wherein said housing has a space below the illuminated test plate, and a reflector is mounted in said space for viewing the underside of the test plate.

7. A target for modifying illumination of a test plate having a multiplicity of individual wells arranged in predetermined order, said target comprising a translucent sheet having on one side a region containing a pattern of individual substantially opaque areas corresponding in number, size and location to the number, size and location of the test plate wells and on the other side a light diffusing surface extending over a region at least coextensive with said region containing the opaque areas.

8. The target defined in claim 7, wherein said light diffusing surface region has a substantially opaque border.

9. A method of illuminating for test purposes a transparent test plate having a multiplicity of spaced individual material containing wells arranged in predetermined pattern, comprising the step of introducing said test plate across a light path between a light source and a viewing station while modifying the light illuminating said plate by blocking the light only in an individual area pattern across the light path corresponding substantially exactly to the pattern of wells of the test plate.

* * * * *